United States Patent [19]
Xu et al.

[11] Patent Number: 5,468,772
[45] Date of Patent: Nov. 21, 1995

[54] TRIPTERININ COMPOUND AND METHOD

[75] Inventors: Ren S. Xu, Palo Alto; Tien W. Wiedmann, Stanford, both of Calif.

[73] Assignee: Pharmagenesis, Inc., Palo Alto, Calif.

[21] Appl. No.: 31,288

[22] Filed: Mar. 10, 1993

[51] Int. Cl.$^6$ ........................................... A61K 31/35
[52] U.S. Cl. ..................... 514/453; 514/825; 549/275; 549/281
[58] Field of Search .................. 549/275, 281; 514/453, 825

[56] References Cited

U.S. PATENT DOCUMENTS 4,005,108  1/1977  Kupchan et al. .................. 549/297

OTHER PUBLICATIONS

Yang, S.-X., et al., "Immunosuppression of Triptolide and Its Effect on Skin Allograft Survival," *Int. J. Immunopharmac.* 14(6): 963–969 (1992).

Briggs, J. D., "A critical review of immunosuppressive therapy," *Immunol. Let.* 29:89–94 (1991).

Chen, K., et al., "Anti-AIDS Agents, 4. Tripterifordin, a Novel Anti-HIV Principle From *Tripterygium wilfordii*: Isolation and Structural Elucidation," *J. Nat. Prod.* 55(1):88–92 (1992).

Huying, S., et al., "Effects of *Tripterygium wilfordii* on the Menstruation of 50 Patients Suffering From Rheumatoid Arthritis—With a Summary of Its Therapeutic Effects in 12 Cases of Menorrhagia," *J. Trad. Chin. Med.* 4(3):237–240 (1984).

Juling, G., et al., "*Tripterygium wilfordii* Hook f in Rheumatoid Arthritis and Ankylosing Spondylitis," *Chin. Med. J.* 94(7):405–412 (1981).

Keown, P. A., "Annual Review of Transplantation," from *Clinical Transplants* 1991 (P. Terasaki, Ed., UCLA Tissue Typing Laboratory, Los Angelos, California), pp. 205–223.

Li, X. W., and Weir, M. R., "Radix *Tripterygium Wilfordii*—A Chinese Herbal Medicine With Potent Immunosuppressive Properties," *Transplantation* 50(1):82–86 (1990).

Meifang, C., et al., "Treatment of Chronic Nephritis with Tripterygium Hypoglaucum," *J. Trad. Chin. Med.* 3(3):219–222 (1983).

*Primary Examiner*—C. Warren Ivy
*Assistant Examiner*—Amelia Owens
*Attorney, Agent, or Firm*—Vincent M. Powers; Peter J. Dehlinger

[57] ABSTRACT

An immunosuppressive compound having the structural formula:

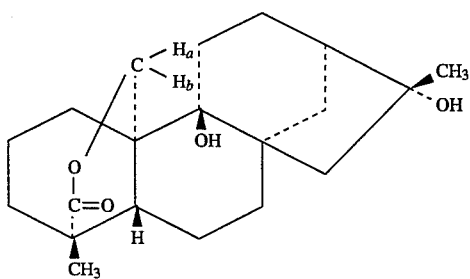

is disclosed, along with immunosuppression treatment methods which employ the compound.

7 Claims, 9 Drawing Sheets

TRIPTERININ COMPOUND AND METHOD

FIELD OF THE INVENTION

The present invention relates to purified tripterinin and an immunosuppression treatment method employing the compound.

REFERENCES

Abbas, A. K., et al., *Cellular and Molecular Immunology*, W. B. Sanders Co. (1991).

Altomonte, L., et al., Clin. Rheumatology, 11(2):202 (1992).

Boyum., A., Scan J. Lab Invest, 21:77 (1968).

Brahn, E., et al., Lymphokine and Cytokine Res. 11(5):253 (1992).

Brennan F. M., et al., British Journal of Rheumatology, 31(5):293-8. (1992)

Briggs J. D., Immunology Letters Jul. 29(1-2):89-94 (1991).

Brozik, M., et al., J. Rheumatology, 19(1):63 (1992).

Catalano, M. A., J. Cellular Biochemistry Supplement 17B:128 (1993)

Chen, K., et al., J. Nat Products, 55(1):88 (1992).

Chin, J. E., et al., Arthritis and Rheumatism 33:1776–1786 (1990).

Chu, C. Q., et al., British J. Rheumatology 31(10):653–661 (1992).

Danis, V. A., et al., Ann. Rheumatic Diseases, 51(8):946 (1992).

Dasgupta, B., et al., J. Rheumatology, 19(1):22 (1992).

DeBennedetti, F., et al., Arth. and Rheumat., 34(9):1158 (1991).

DeBennedetti, F., et al., Clin. & Exp. Rheumatol., 10(5):493 (1992).

Deleuran, B. W., et al., Arth. and Rheumat., 35(10):1180 (1992).

Elliott, M. J., et. al., J. Cellular Biochemistry Supplement 17B: 145 (1993).

Falus, A., et al., Scand. J. Rheumatol. 21(3):116 (1992).

Gilman, S. C., et al., Arthritis and Rheumatism 31:126–130 (1988).

Green, L. M., et al., J. Immunol Methods 70:257 (1984).

Guerne, P. A., et al., J. Clin. Invest. 83:585–592 (1989).

Harigai, M., et al., J. Clin. & Lab. Immun. 34:107–113 (1991).

Holt, I., et al., Eur. J. Clin. Invest., 21(5):479 (1991).

Holt, I., et al., Brit. J. Rheumatology, 21(11):725 (1992).

Keown, P. A., Ann. Rev. Trans., Clin. Transplants 205–223, (1991).

Kishimoto, T., J. Autoimmunity, 5 Supp. A:123 (1992).

Koch, A. E., et al., Clin. Immunol. & Immunopath. 65:23–29 (1992).

Li, X. W., et al., Transplantation 50:82 (1990).

McCachren, S. S., et al., Arthritis and Rheumatism 32:1539–1545 (1989).

Mishell, B., et al., eds., *Selected Methods in Cellular Immunology*, Freeman and Co. (1980).

Noelle, R. J., et al., FASEB 5(13):2770 (1991).

O'Gara, A. and Defrance, T.: "Bioassays for interleukins", In *Laboratory Methods in Immunology*, H. Zola, Ed. CRC Press (1990).

O'Neill, L. A., et al., European J. Pharmacol. 166:131–137 (1989).

Platt, J. L., et al., Immunol. Today 11(2):450 (1990).

Roberts, J. P., et al., Ann. Rev. Med., 40:287 (1989).

Roitt, I., *Essential Immunology*, 7th edition, Blackwell Sci Pub, p. 63 (1991).

Sawada, T., et al., Clin. and Exp. Rheumatology 9(4):363 (1991).

Schumacher, H. R. ed., *Pimer on the Rheumatic Diseases*, Ninth edition, Arthritis Foundation, Atlanta, Ga. (1988).

Smith, J. B., et al., Rheumatology Int'l 9(2):53–58 (1989).

Tan, P. L., et al., J. Rheumatol., 17(12):1608 (1990).

Thompson, R. C., et al., Int'l J. Immunopharmacol. 14:475–480 (1992).

Vivian, B., et al., Biotherapy 4:317–323 (1992).

Watson. J., et al., J. Exp. Med. 150:849 (1979).

Williams, N. C., et al., Clin. & Exp. Immunol., 87(2):183 (1992).

Wood, N. C., et al., Clin. & Exp. Immunol., 87(2):183 (1992).

Yamamura, M., et al., Acta Medica Okayama 44(6):301–308 (1990).

BACKGROUND OF THE INVENTION

A. Autoimmune Disease

The immune system functions as the body's major defense against diseases caused by invading organisms. This complex system fights disease by killing invaders such as bacteria, viruses, parasites or cancerous cells while leaving the body's normal tissues unharmed. The immune system's ability to distinguish the body's normal tissues, or self, from foreign or cancerous tissue, or non-self, is an essential feature of normal immune system function. The loss of recognition of a particular tissue as self and the subsequent immune response directed against that tissue produces serious illness. An autoimmune disease results from the immune system attacking the body's own organs or tissues, producing a clinical condition associated with the destruction of that tissue. An autoimmune attack directed against the joint lining tissue results in rheumatoid arthritis; an attack against the conducting fibers of the nervous system results in multiple sclerosis.

Rheumatoid arthritis is one of the most common of the autoimmune diseases. Current treatments include three general classes of drugs (Schumacher, 1988): antiinflammatory agents (aspirin, non-steroidal antiinflammatory drugs and low dose corticosteroids); disease-modifying antirheumatic drugs, known as "DMARDs" (antimalarials, gold salts, penicillamine, and sulfasalazine) and immunosuppressive agents (azathioprine, chlorambucil, high dose corticosteroids, cyclophosphamide, methotrexate, nitrogen mustard, 6-mercaptopurine, vincristine, hydroxyurea, and cyclosporin A). The autoimmune diseases share a common underlying pathogenesis and the need for safe and effective therapy. None of the available drugs are completely effective, and most are limited by severe toxicity.

Recent research has established that rheumatoid arthritis and other autoimmune diseases are associated with specific cytokine abnormalities. A growing body of evidence supports the notion that IL-1 is a key mediator of inflammation in rheumatoid arthritis (RA). Elevated levels of IL-1 have been reported in synovial fluid obtained from rheumatoid arthritic joints (Smith, et al.), peripheral blood lymphocytes from RA patients have been shown to produce supranormal amounts of IL-1 in culture (Yamamura, et al.), and IL-1 has been detected at the cartilage-pannus junction (Chu, et al.), the anatomic site of articular cartilage destruction. IL-1 has been shown to increase the production of other biochemical mediators of joint inflammation, including intercellular adhesion molecules (Chin, et al.), IL-6 (Harigai, et al.; Guerne, et al.), prostaglandin E2 (O'Neill, et al.), phospholipase A (Gilman, et al.) and metalloproteases (McCachren, et al.). Macrophages isolated from the synovium of rheumatoid arthritic joints express both the IL-1 gene and the IL-1 receptor antagonist gene, indicating that an imbalance between the cytokine and its endogenous antagonist may play an etiologic role in the disease (Koch, et al.).

Investigators have shown that TNFα (tumor necrosis factor-α) also plays a significant role in the pathology of rheumatoid arthritis (Brennan). TNFα increases the severity of collagen induced arthritis in animal models (Brahn) while anti-TNFα antibody administration ameliorates collagen induced arthritis (Williams; et al.). TNFα is increased in the serum of RA patients (Holt, et al., 1992; Altomonte, et al., 1992), and both the cytokine (Chu, et al.) and its receptors have been identified in rheumatoid synovium, at the cartilage-pannus junction (Deleuran, et al.). Serum levels of both IL-1 and TNFα decline in RA patients following long term administration of the disease modifying drug sulfasalazine (Danis, et al.), suggesting that the concentrations of these cytokines reflect the clinical course of the disease.

Interleukin 6 (IL-6) is a third cytokine that appears to play a major role in the development of RA. Supranormal concentrations of this cytokine are found in both the serum (Wood, et al.; Holt, et al.) and the synovial fluid of RA patients. Synovial fluid IL-6 levels are increased during active disease (Brozik, et al.; Dasgupta, et al.; DeBennedetti, et al.), but not during remission (DeBennedetti, et al.). IL-6 concentrations vary in direct proportion to the circulating levels of IgM, IgG and IgA rheumatoid factors, but not to the total circulating levels of IgM, IgG and IgA (Sawada, et al.). IL-6 is found at the at the cartilage-pannus junction (Chu, et al.). Both synovium (Falus, et al.) and cultured synovial cells (Tan, et al.; Guerne, et al.) from RA patients produce IL-6 in vitro. The supranormal concentration of IL-6 may be an important factor in the stimulation autoantibody production (Kishimoto).

Recognition of the important role of these cytokines in autoimmune disease has fostered the development of a new generation of therapeutic agents. Proteins such as monoclonal antibodies and soluble receptors targeted against IL-1 and TNFα are currently being evaluated in clinical trials for the treatment RA and other autoimmune diseases. Preliminary results of administration of anti-IL-1 monoclonal antibodies to a small group of rheumatoid patients suggest improvement in both the clinical and laboratory manifestations of the disease (Catalano). Administration of monoclonal antibodies to TNFα has also shown encouraging early results in a group of nine patients with severe RA (Elliott).

Therapies seeking to modulate cytokine activity show promise for the treatment of autoimmune disease, but their use may prove impractical. As described above, these complex diseases are characterized by multiple cytokine abnormalities. Effective treatment could require the simultaneous administration of several agents, each targeting a specific cytokine pathway. Administration of even a single protein is likely to be limited by the potential immunogenicity of these large molecules, the need for intravenous administration and the relatively high costs of protein production.

The ideal drug for treatment of an autoimmune disease would be a plieotrophic agent that acts on each of the known aberrant cytokine pathways. In the case of rheumatoid arthritis, such a drug would inhibit IL-1, TNFα and IL-6. The development of an orally active compound that specifically modifies the production or action of these cytokines would offer a practical, cost effective contribution to the new generation of cytokine modifying drugs.

B. Organ Transplantation

Organ transplantation involving human organ donors and acceptors (allogeneic grafts) and more recently, involving non-human primate donors and human acceptors (xenogeneic grafts) has received considerable medical and scientific effort over the past two decades (Keown; Roberts; Platt). To a great extent, this effort has been aimed at eliminating, or at least reducing, the problem of transplantation rejection by the host immune system, leading to the destruction of the transplanted organ.

From follow-up studies on human transplant patients, as well as transplantation studies in animal model systems, the following features of transplantation rejection have been established. The major targets in transplant rejection are non-self allelic forms of class I and class II major histocompatibility complex (HMC) antigens (Roitt). Rejection is mediated by both antibodies and cytolytic T lymphocytes (CTLs), with the participation of CD4+ "helper" T cells (Noelle). In general, foreign class I MHC antigens stimulate CD8+ CTLs, and foreign class II MHC antigens stimulate CD4+ T cells (Roitt).

Presently, the most commonly used agents for preventing transplantation rejection include corticosteroids, cytotoxic drugs that specifically inhibit T cell activation, such as azathioprine, immunosuppressive drugs, such as cyclosporin A, and antibodies specific against donor organ foreign antigens (Briggs). All of these drug therapies are limited in effectiveness. In addition, the doses needed for effective treatment of transplantation may increase the patient's susceptibility to infection by a variety of opportunistic invaders.

SUMMARY OF THE INVENTION

The invention includes, in one aspect, a purified compound for use in immunosuppressive therapy, named tripterinin, having the structural formula:

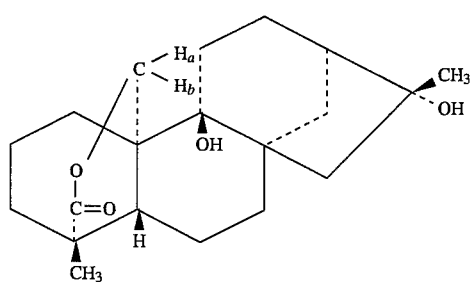

In another aspect, the invention includes a pharmaceutical composition for use as an immunosuppressive agent. The composition includes purified tripterinin in a pharmaceutically acceptable delivery vehicle. The composition may further include cyclosporin A, azathioprine, methotrexate or a glucocorticoid.

As discussed above, a large body of research suggests that IL-1, IL-6 and TNFα play a significant role in the pathology of rheumatoid arthritis and other autoimmune diseases. According to one aspect of the invention, it has been discovered that purified tripterinin acts to suppress the action of IL-1 as well as the production of TNFα and IL-6.

The invention includes, in one aspect, a method of treating rheumatoid arthritis in a patient. The method includes administering to a patient, an amount of tripterinin which is effective to reduce serum or synovial fluid activity levels of one or more of the cytokines IL-1, TNFα, or IL-6.

More generally, the invention includes a method of treating an autoimmune disease characterized by increased serum or synovial fluid activity levels of IL-1, IL-6, and/or TNFα. The method includes administering to the patient, an amount of the compound effective to reduce serum or synovial fluid activity levels of one or more of the cytokines IL-1, TNFα, or IL-6.

In both methods above, the tripterinin compound may be administered in combination with cyclosporin A, azathioprine, methotrexate, or a glucocorticoid.

Also disclosed is a method for treating transplant rejection in a subject, by administering to the subject, a therapeutically effective amount of purified tripterinin, or tripterinin in combination with cyclosporin A, azathioprine, methotrexate, or a glucocorticoid.

These and other objects and features of the invention will become more fully apparent when the following detailed description of the invention is read in conjunction with the accompanying drawings.

DETAILED DESCRIPTION OF THE INVENTION

I. Purified Tripterinin

Figure 1A:
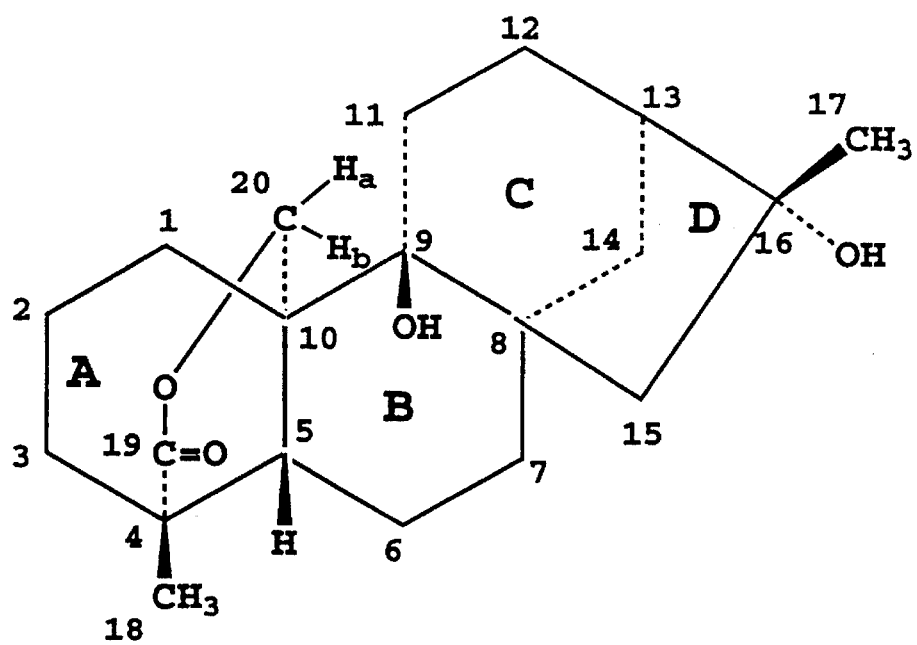
FIGS. 1A and 1B show the structure of tripterinin seen from a "top" view (1A) and rotated 90° to show a side view (1B)

In one aspect, the invention includes a purified diterpene compound isolated from Tripterygium wilfordii. The compound has the structural formula given in FIGS. 1A and 1B, and is designated herein as "tripterinin" after its source.

A. Purification of Tripterinin

The compound is purified from a T. wilfordii extract prepared as follows: The extract is obtained from the root xylem of Tripterygium wilfordii, a medicinal plant which is grown in the Fujiang Province and other southern provinces of China. Plant material can be obtained easily in China. The preparation of the extract is detailed in Example 1. Briefly, dried plant material is ground into a crude powder and extracted with 95% ethanol with refluxing. Repeated ethanol extracts are combined, filtered and reduced to a syrupy extract.

This extract is diluted with water, and methylene chloride-soluble components are extracted in methylene chloride. Following concentration, the methylene chloride extract is applied to a silica gel column, then eluted successively with methylene chloride and methylene chloride:methanol (95:5). The fractions which elute with 95:5 methylene chloride:methanol are combined. This crude extract is referred to as a 1:1000 extract, based on the yield of product.

The 1:1000 extract is purified using silica gel chromatography, to yield, after one purification cycle on silica gel, a 1:5000 extract, and after a second purification cycle, a 1:10000 purification extract.

The 1:10000 extract from above was dissolved in methylene chloride, applied to a Lobar column (Type B, Si 60) and eluted with a hexane:methylene chloride:methanol mixture, yielding 24 elution fractions. Crystalline tripterinin appeared in fractions 17 and 18. The compound was recrystallized in acetone:ethyl ether. Yield of the final step was 0.78%; 640 mg of the 1:10,000 extract yielded 5 mg of white needles, melting point 450° C.

Figure 2:
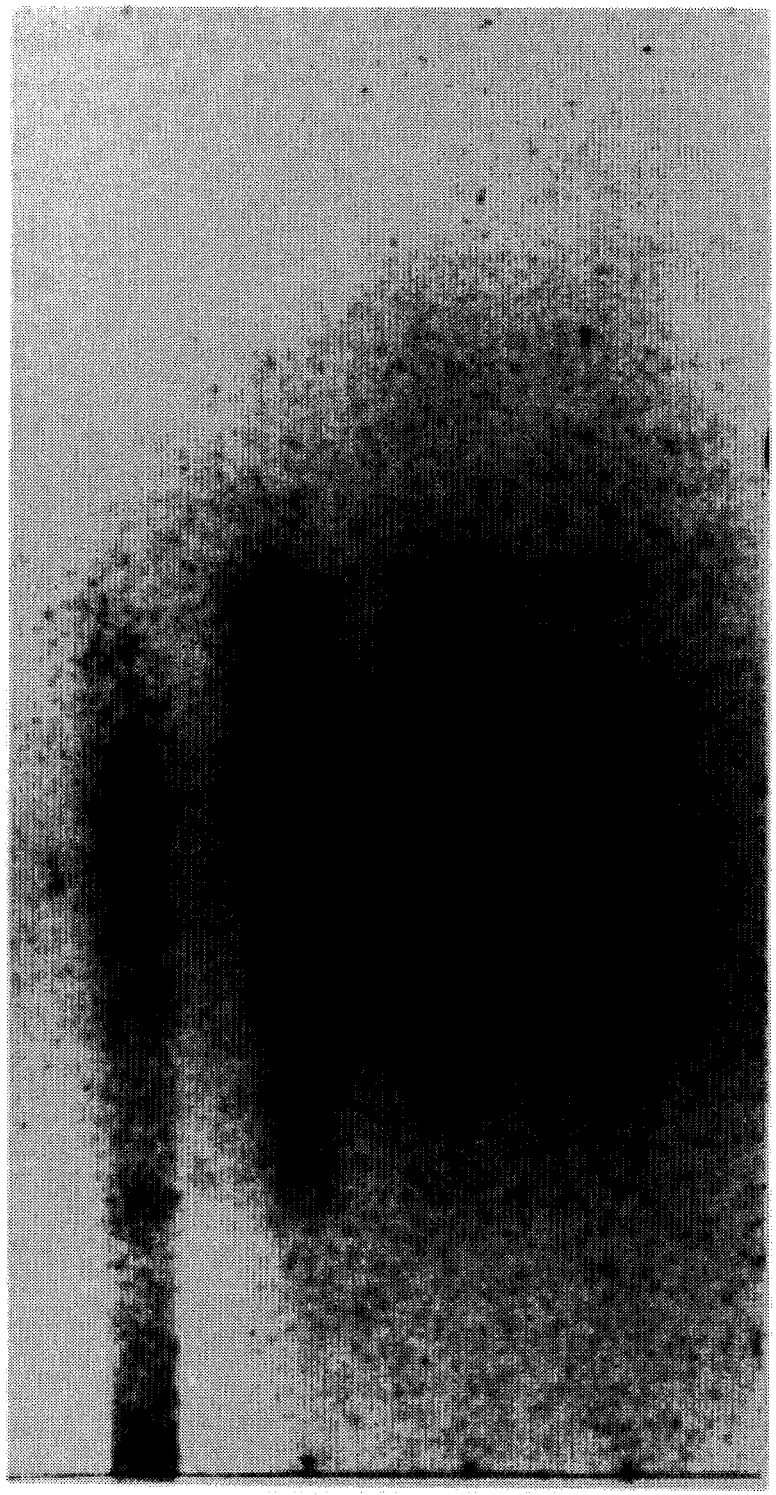
FIG. 2 shows a TLC chromatogram of a 1:1,000 Tripterygium wilfordii extract (lane A), a 1:5,000 extract (lane B), a 1:10,000 extract (lane C), and purified tripterinin (lane D)

Crystalline tripterinin dissolved easily in methylene chloride or acetone. The compound produced a strong pink color on thin layer chromatography (developed with vanillin:sulfuric acid as described in Example 2). FIG. 2 shows a thin layer chromatogram of the various extracts. As seen from a comparison of the lanes, purification between the 1:1000 (lane A), 1:5000 (lane B), 1:10000 (lane C), the extracts were successively enriched for compound(s) having the migration characteristics of the purified tripterinin compound (lane D). The final purified product showed no contaminant bands.

B. Structural Analysis

Figure 1B:
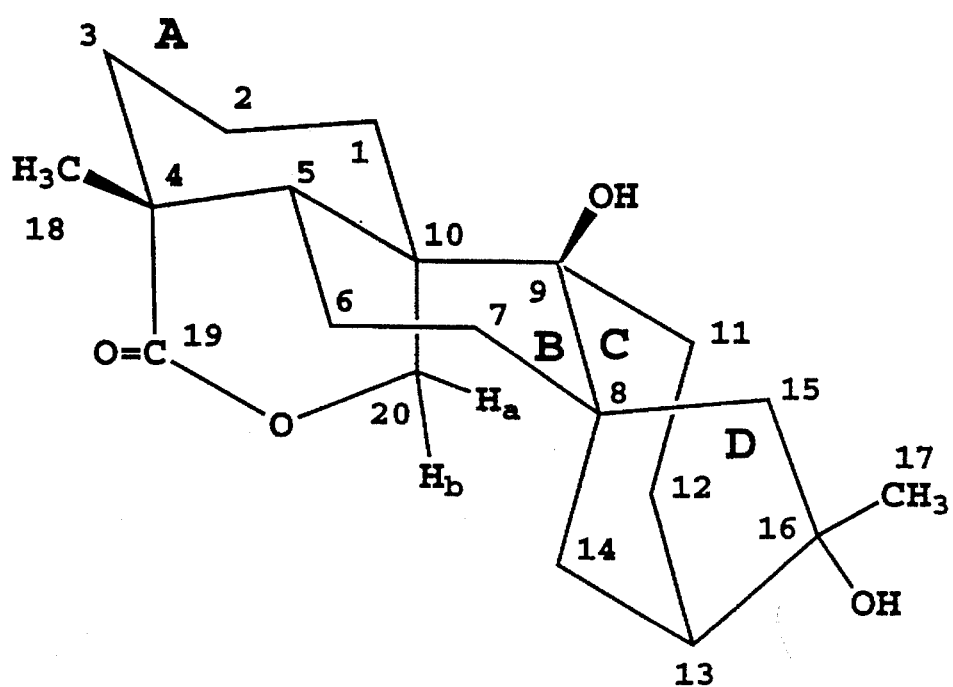

FIGS. 1A and 1B show the structure of the tripterinin compound of the invention, in a "top" and a 90° rotated "side view", respectively. The compound has a diterpene structure, with positions of the 20 carbon atoms identified as shown. The compound has a kaurane backbone (composed of rings A, B, C, and D), and a lactone ring formed across the 4 and 10 carbon positions of ring A, and is hydroxylated at the 19 position.

Figure 3:
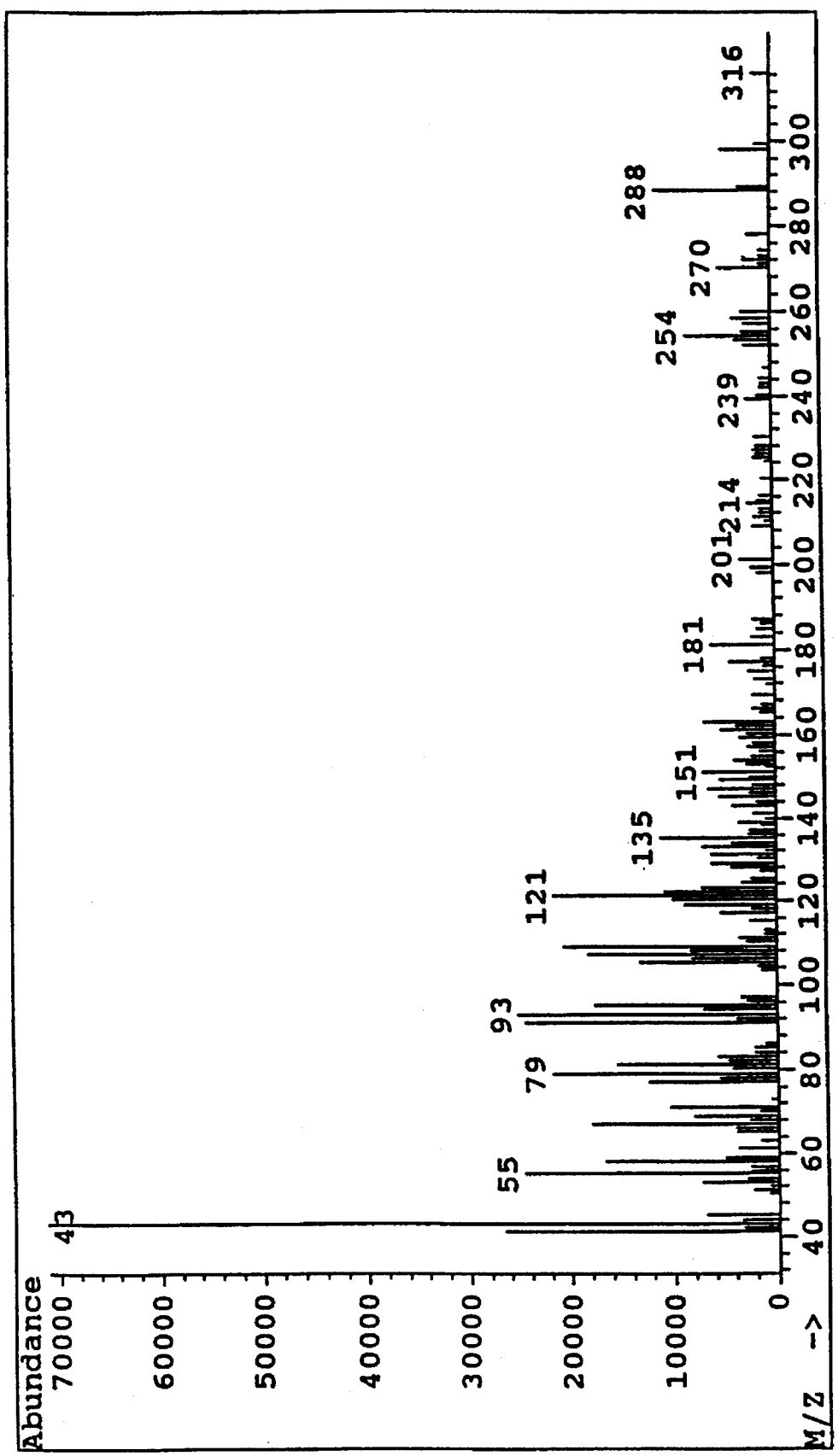
FIG. 3 shows the abundance distribution of ionic fragments generated by high-resolution mass spectroscopy of tripterinin.
Figure 4:
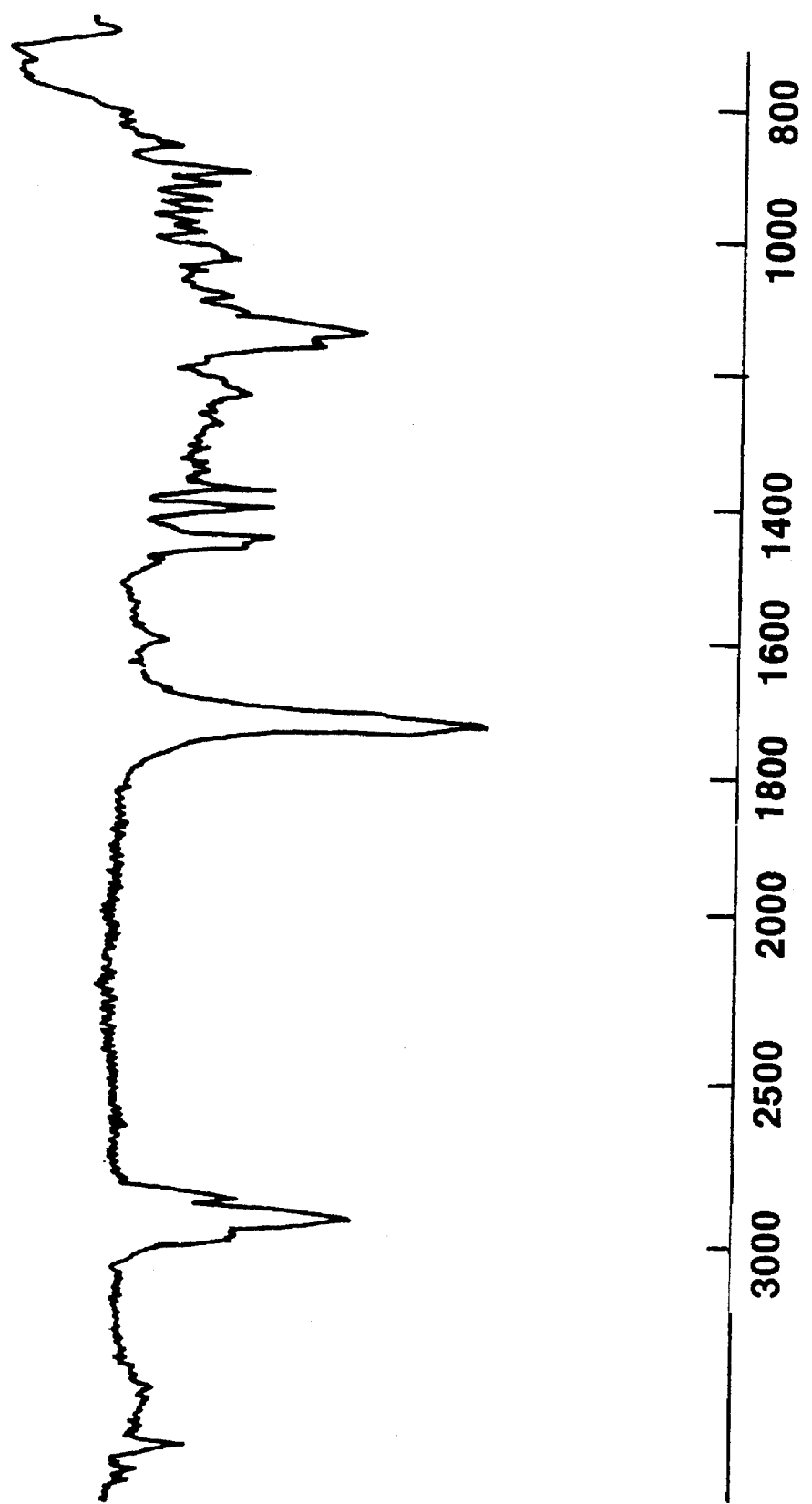
FIG. 4 shows an IR spectrum of tripterinin.
Figure 5:
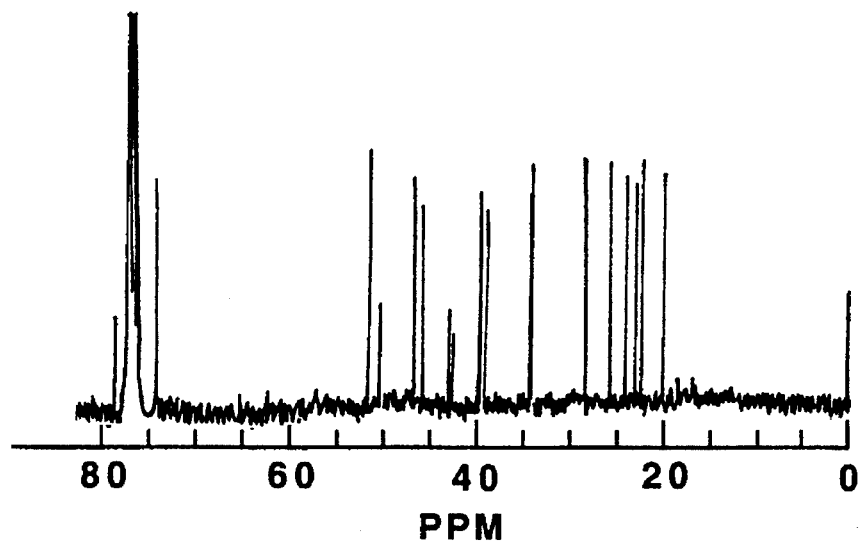
FIG. 5 shows the $^{13}C$ NMR spectrum of tripterinin.

The high resolution mass spectrum indicated the compound's molecular formula to be $C_{20}H_{30}O_4$ (MH$^+$ 335.222620, Calc. 335.222351). The relative abundance of mass fragments is shown in FIG. 3. The distribution of mass spectral fragments, m/z 317.3 (MH$^+$-H$_2$O), and 299.3 (MH$^+$ -2 H$_2$O) suggests that the compound contains two hydroxyl groups. This is confirmed by infrared absorption peaks at 3600 and 3440 cm$^{-1}$ (FIG. 4). The strong absorption peaks at 1720 cm$^{-1}$ and 1140 cm$^{-1}$ represent two other oxygen atoms in a d-lactone ring. The presence of the lactone ring is further confirmed by the $^{13}$C-NMR signal at δ1.76.4 (FIG. 5).

Figure 6A:
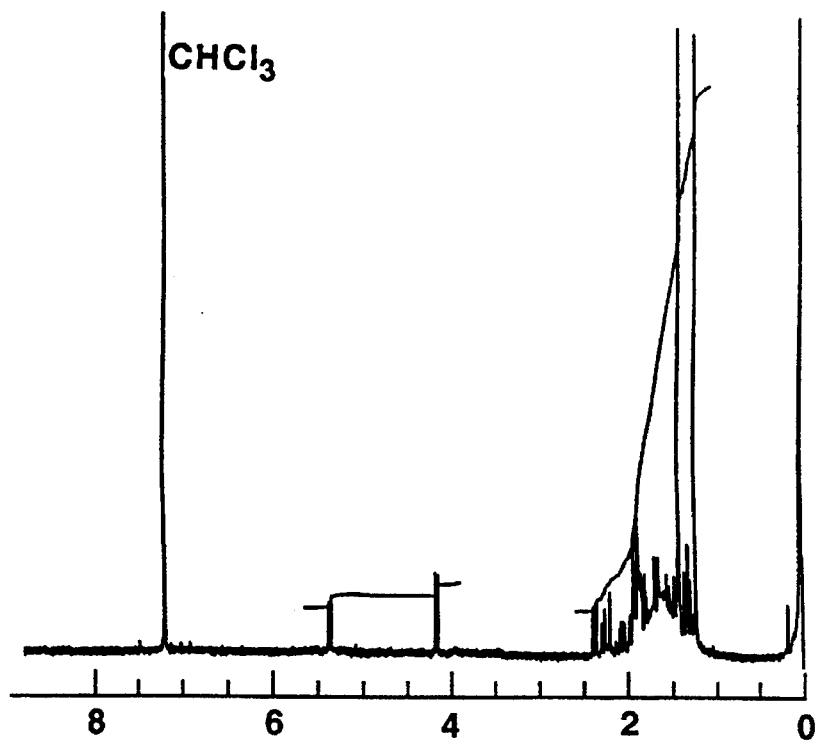
FIGS. 6A and 6B show the proton NMR spectrum of tripterinin in chloroform (6A), and the expanded spectrum over the 1–2.4 ppm region of the spectrum (6B)
Figure 6B:
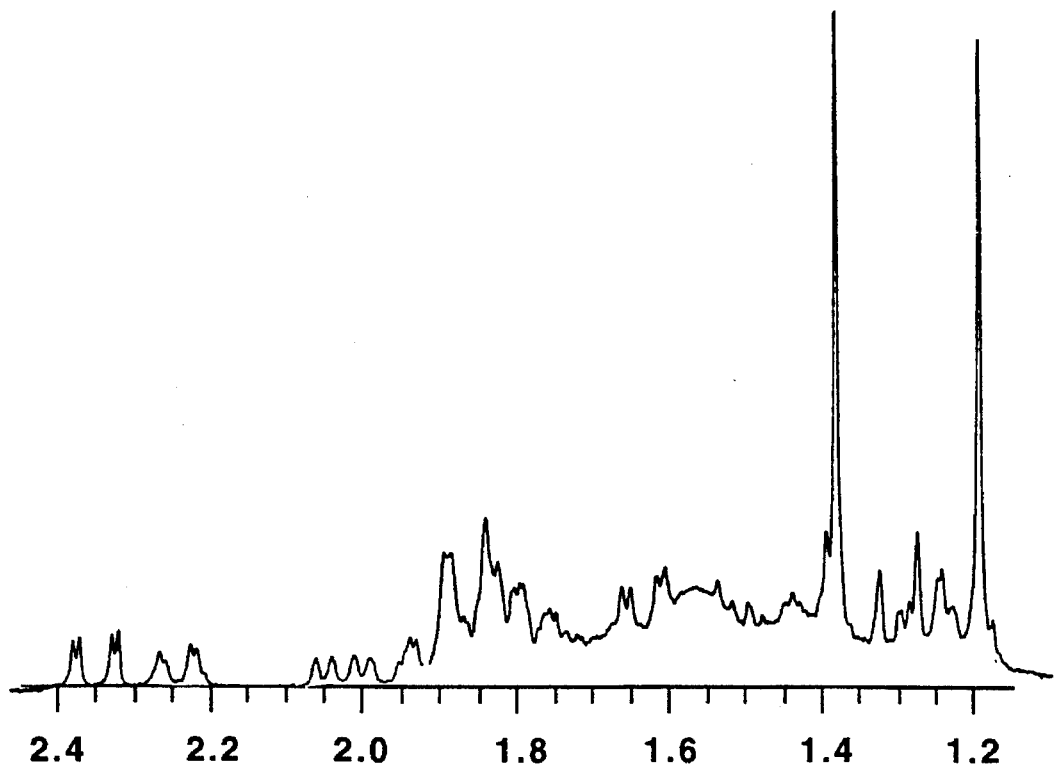

The $^1$H-NMR spectrum (FIGS. 6A and 6B) shows two proton signals at δ5.37 (dd, J=14,2) and 4.13 (dd, J=14,1) implying oxymethylene functions, and two methyl signals at δ1.40 and 1.20 (each in singlet). The other signals are concentrated in the d 1.2–2.4 ppm area; this implies that both hydroxyl groups are located at quaternary carbons.

The $^{13}$C-NMR spectrum (FIG. 5) indicates the presence of two methyls, ten methylenes, two methines and six quaternary carbons. Taken together, the above data suggest that the compound is a diterpenoid, but with a five ring structure containing a lactone ring and two hydroxyl groups. The carbon signals indicate that the compound likely belongs to the ent-kauran group, by comparison of their carbon signals.

In comparison with other diterpenoids with lactone rings, tripterinin proved similar to tripterifordin, a novel anti-HIV principle also found in *Tripterygium wilfordii* (Chen). Tripterinin differs in that it contains an additional hydroxyl group at position 9.

Comparison of the $^{13}$C-NMR spectra of Tripterifordin and tripterinin shows that tripterinin has relative downfield shifts at C-8 (δ5.6 ppm), C-10 (δ4.4 ppm), and C-11 (δ11.3 ppm) and upfield shifts at C-5 (δ5.4 ppm), C-7 (δ5.1 ppm), C-14 (δ3.5 ppm), and C-15 (δ6.2 ppm) (Table 1). The data indicate that tripterinin is similar in structure to tripterifordin, but has a single additional hydroxyl group at C-9.

TABLE 1

Carbon Resonance Shift Assignments For Tripterinin and Tripterifordin d$^{13}$C (ppm)

| Position | Tripterinin | | Tripterifordin | |
|---|---|---|---|---|
| 1 | 40.0 | t | 40.6 | t |
| 2 | 20.4 | t | 20.9 | t |
| 3 | 39.0 | t | 40.6 | t |
| 4 | 42.8 | s | 43.0 | s |
| 5 | 45.8 | d | 51.2 | d |
| 6 | 22.8 | t | 22.4 | t |
| 7 | 34.6 | t | 39.7 | t |
| 8 | 50.4 | s | 44.8 | s |
| 9 | 74.4 | s | 50.3 | d |
| 10 | 43.1 | s | 38.7 | s |
| 11 | 28.8 | t | 17.5 | t |
| 12 | 26.1 | t | 26.0 | t |
| 13 | 46.8 | d | 48.2 | d |
| 14 | 34.4 | t | 37.9 | t |
| 15 | 51.6 | t | 57.8 | t |
| 16 | 79.1 | s | 79.0 | s |
| 17 | 23.3 | q | 24.5 | q |
| 18 | 24.4 | q | 23.5 | q |
| 19 | 176.4 | s | 176.5 | s |
| 20 | 74.6 | t | 73.9 | t |

Figure 7:
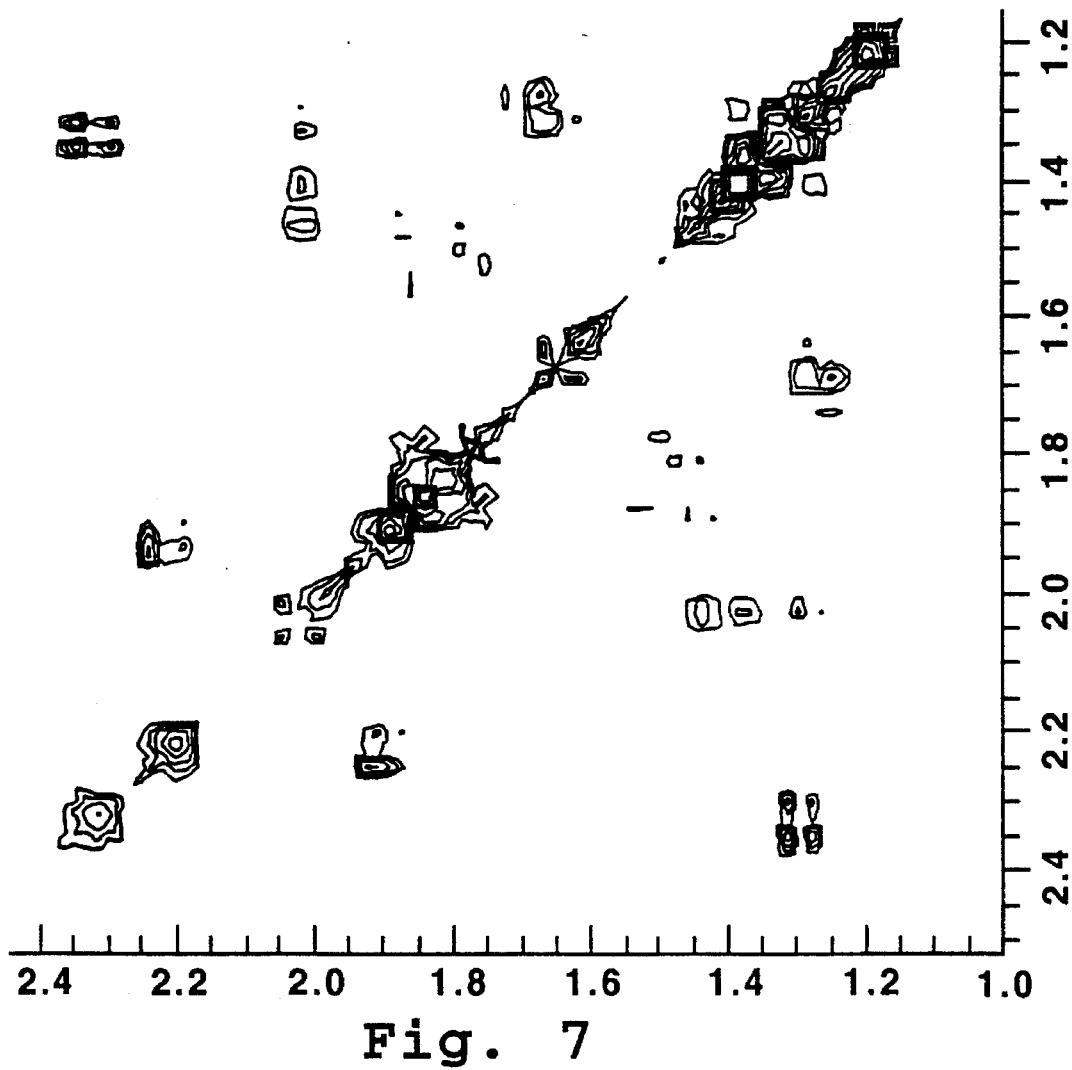
FIG. 7 shows a 2-D proton-proton NMR COSY spectrum of tripterinin, in an expanded 1–2.4 ppm region of the spectrum.

Some proton signals could be assigned according to the $^1$H-$^1$H COSY spectrum (FIG. 7). Cross peaks are seen between: H-1 a (δ2.34, dd, J=2.6, 12.6) and H-1b (δ1.28, m); H-14 a (δ2.24, ddd, J=2.7,4,9.8) and H-14 b (δ1.92, dd, J=2,9.8); H-13 (d 2.04, ddd, J=1.2, 5.2, 12) and H-12 b (δ1.42, m) H-12 a (δ1.32, m), H-3 a (δ1.83, dd, J=3.5, 10) and H-3 b (δ1.76, m) H-6 b (δ1.65, J=3, 11.5) and H-6 a (δ1.25, m)

The NOESY spectrum showed NOE between protons H-20 a (δ4.13) and H-1 a (δ2.34), and between CH$_3$-18 (δ1.20) and H-3 b (δ1.76). On the basis of above spectral data and comparison with tripterifordin, the structure of tripterinin shown in FIG. 1A was determined.

C. Compound Formulations

When the purified compound is employed in the form of solid preparations for oral administration, the preparations may be tablets, granules, powders, capsules or the like. In a tablet formulation, the compound is typically formulated with additives, for example, an excipient such as a saccharide or cellulose preparation, a binder such as starch paste or methyl cellulose, a filler, a disintegrator and so on, all being ones usually used in the manufacture of medical preparations.

For use in oral liquid preparation, the compound may be prepared as a liquid suspension, emulsion, or syrup, being supplied either in liquid form or a dried form suitable for hydration in water or normal saline.

The compound of the present invention may be injected in the form of aqueous solutions, suspensions or oily or aqueous emulsions, such as liposome suspensions. Typically, for parenteral administration, the extract is formulated as a lipid, e.g., triglyceride, or phospholipid suspension, with the extract components being dissolved in the lipid phase of the suspension.

As will be described below, the tripterinin compound is also intended for use in combination with an immunosuppressive drug, such as cyclosporin A, azathioprine, methotrexate or a glucocorticoid. The invention also includes a composition containing tripterinin in combination and one of these drugs. One preferred composition contains tripterinin and cyclosporin A.

II. Cytokine Inhibitory Activity

Purified tripterinin was examined for immunosuppressive activity in a variety of in vitro biological assays.

A. Anti-Proliferative Effect on Human PBL's in vitro

One measure of immunosuppression is suppression of stimulated peripheral blood lymphocyte (PBL) proliferation in vitro. In the assay detailed in Example 3, PBLs were activated in vitro by addition of anti-CD3 monoclonal antibody (X-35 antibody). At the same time, purified tripterinin or vehicle (control) was added to each culture, at selected concentrations. After 72 hours incubation, tritiated thymidine was added to the culture medium, and thymidine incorporation into DNA was assayed, as a measure of DNA synthesis associated with cell proliferation.

Figure 8:
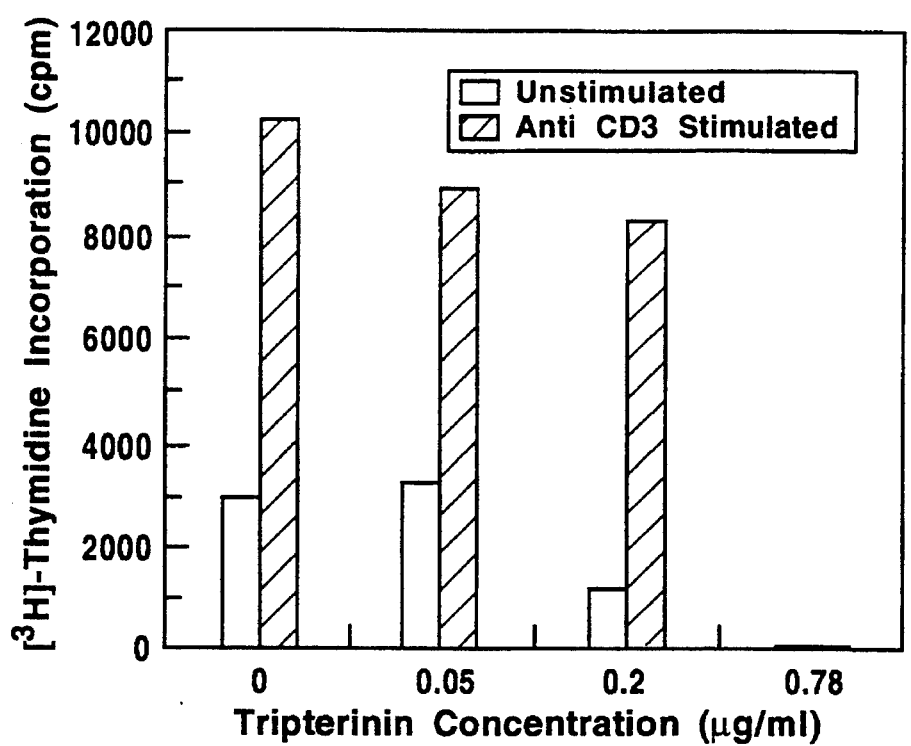
FIG. 8 shows inhibition of human peripheral blood lymphocyte proliferation by tripterinin in the absence (solid bars) and the presence (crosshatched bars) of anti CD3 antibody.

FIG. 8 shows inhibition of peripheral blood lymphocyte proliferation, in the presence (crosshatched bars) and absence (solid bars) of stimulation with anti CD3 antibody, as a function of concentration of added tripterinin. As seen, increasing amounts of purified tripterinin produced dose dependent inhibition of proliferation of both unstimulated and anti-CD3 stimulated PBLs, with substantially complete inhibition occurring at a dose of 0.78 μg/ml tripterinin.

The specific activity of tripterinin (on a weight basis) for inhibition of PBL proliferation in the presence of CD3 antibody was compared with that of a structurally related compound, tripterifordin. This compound differs in structure from tripterinin by the presence of an H, rather than an OH, group at the position-19 carbon in the FIG. 1a structure (Chen).

Figure 9:
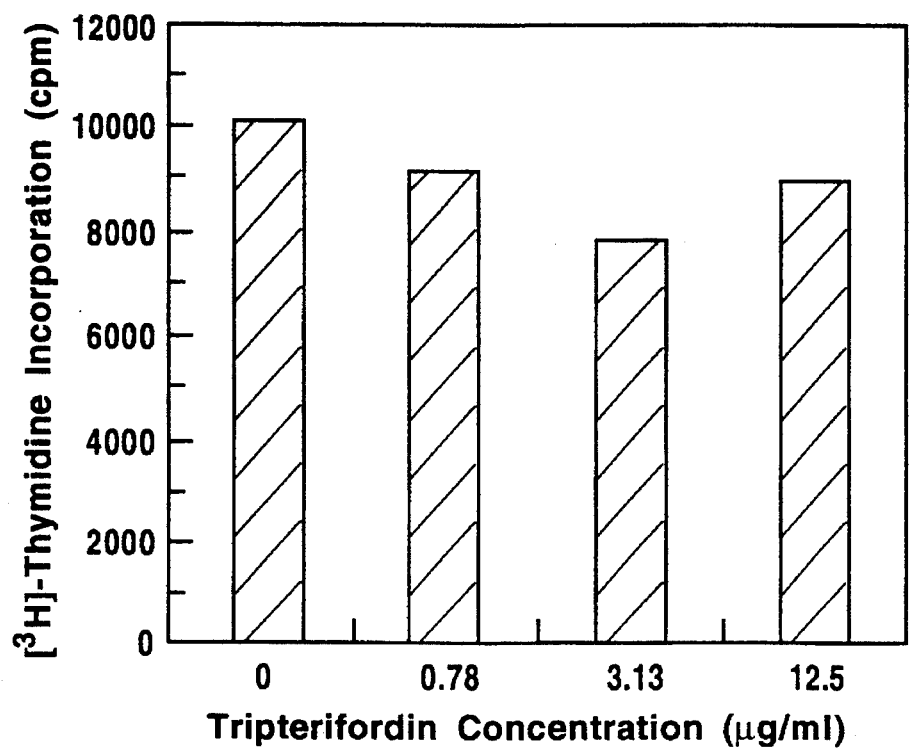
FIG. 9 shows the lack of inhibition of peripheral blood lymphocyte proliferation by tripterifordin in the presence of anti CD3 antibody.

The ability of tripterifordin to inhibit anti-CD3 stimulated PBL proliferation was assayed at concentrations of 0, 0.78, 3.13, and 12.5 μg/ml, with the results shown in FIG. 9. As seen, tripterifordin failed to significantly inhibit PBL proliferation at the highest concentration of compound tested.

B. Inhibition of IL-1 Action

According to one important aspect of the invention, it has been discovered that tripterinin has the ability to inhibit IL-1 stimulated lymphocyte cell proliferation. The implications of this finding, for use in immunosuppression therapy, are discussed in Section III below.

The ability of tripterinin and tripterifordin to suppress the cell-proliferative effect of IL-1 in mouse thymocytes, an index of IL-1 action (O'Gara), was also examined. In this study, mouse thymocytes in culture were stimulated with IL-1 in the presence of phytohemagglutinin (PHA) and increasing concentrations of purified tripterinin or tripterifordin. The cells were cultured for 72 hours, and during the last four hours, incubated with tritiated thymidine. DNA synthesis was assessed by measurement of radiolabeled thymidine incorporation.

Figure 10:
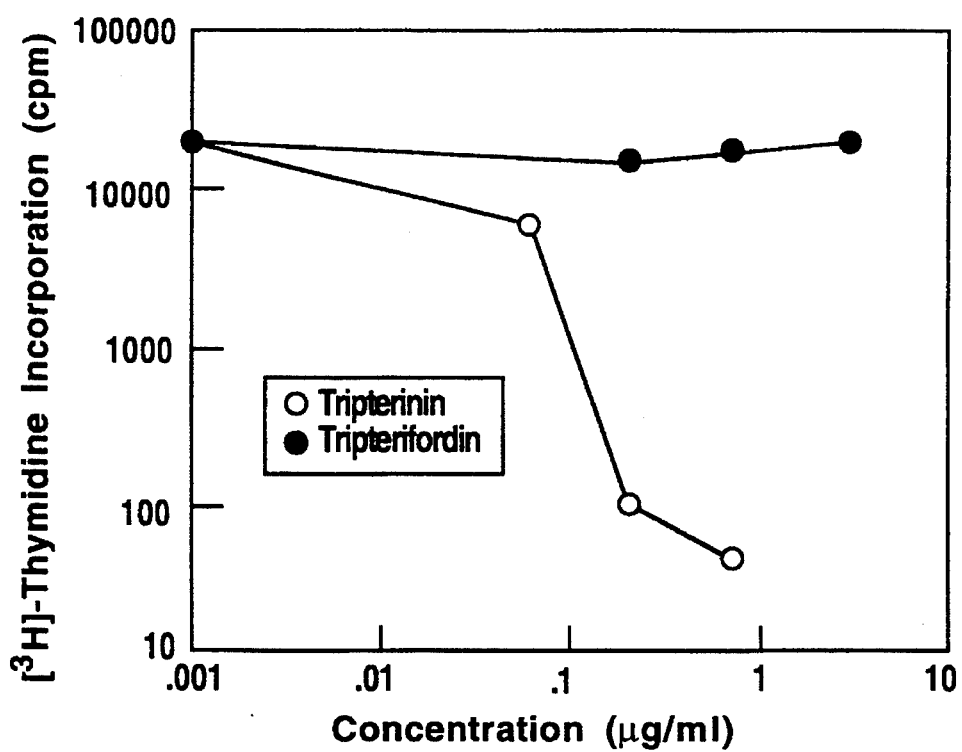
FIG. 10 compares the effect of tripterinin (open circles) and tripterifordin (closed circles) on IL-1 mediated stimulation of mouse thymocyte proliferation.

FIG. 10 shows the inhibition of IL-1 stimulated thymocyte proliferation in culture at concentrations up to 0.78 µg/ml tripterinin and up to 3.13 µg/ml tripteriforfin. As seen in the figure, IL-1 stimulated cell proliferation was inhibited by tripterinin at a concentration of about 0.2 µg/ml with half-maximal inhibition occurring at a concentration of about 0.3 µg/ml. By contrast, little or no inhibitory effect of tripteriforfin was observed, even at a compound concentration of 3.13 µg/ml.

C. Inhibition of IL-2 Action

Figure 11:
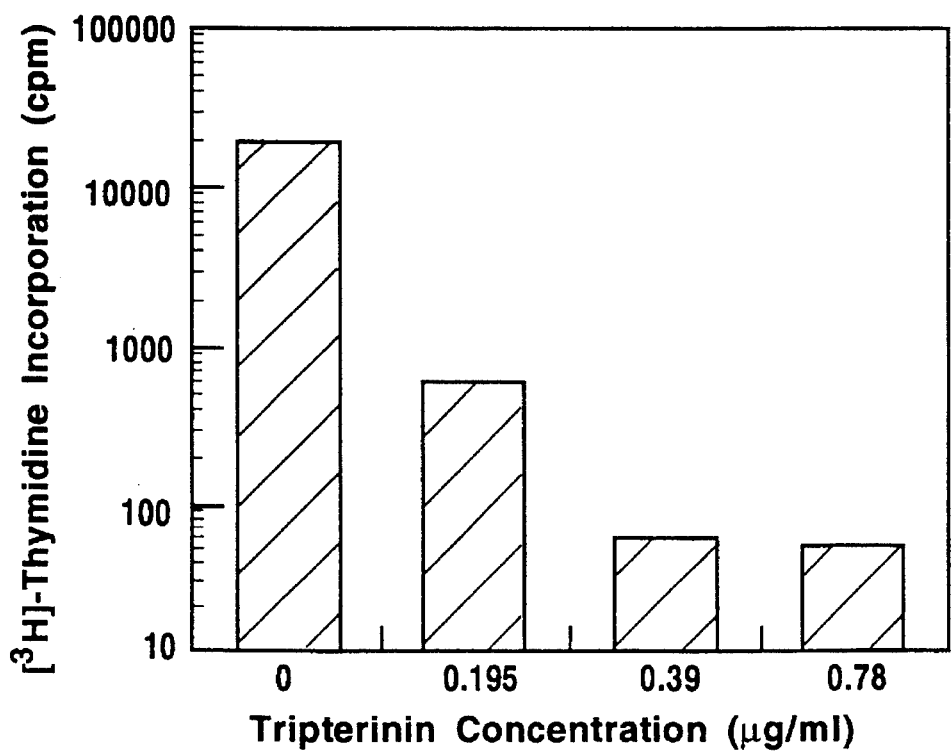
FIG. 11 shows the suppressive effect of tripterinin on IL-2 stimulation of HT-2 cell proliferation.

A similar study showed that tripterinin also blocks the cell-proliferative activity of IL-2 on HT-2 cultured lymphocytes (O'Gara), as detailed in Example 5. Briefly, HT-2 cells were incubated in the presence of IL2, and in the presence of increasing concentrations of tripterinin. After 20 hours incubation, tritiated thymidine was added and the incubation carried out for an additional 4 hours. Cells were harvested and counted as described for PBL proliferation. The results are shown in FIG. 11. The data show a more than 10-fold decrease in cell proliferation, as measured by incorporation of thymidine into DNA, at a tripterinin concentration of 0.4 µg/ml. Half maximal inhibition occurred at about 0.1 µg/ml.

D. Effect on Cytokine Production

The effect of tripterinin on the production of the cytokines IL-1b, IL2, IL-6, IFNγ, and TNFα was assessed by measurement of the concentration of these cytokines in PHA stimulated human PBL cultures. Cytokine levels were measured by standard ELISA methods using commercially available kits, as detailed in Example 6. Briefly, assay buffer was added to each of the wells of a microtiter plate containing pre-bound anti-cytokine antibody, followed by addition of standard or sample solution, diluted appropriately for the cytokine concentration measured, followed by a second reporter-labeled antibody specific against the anti-cytokine antibody.

Figure 12:
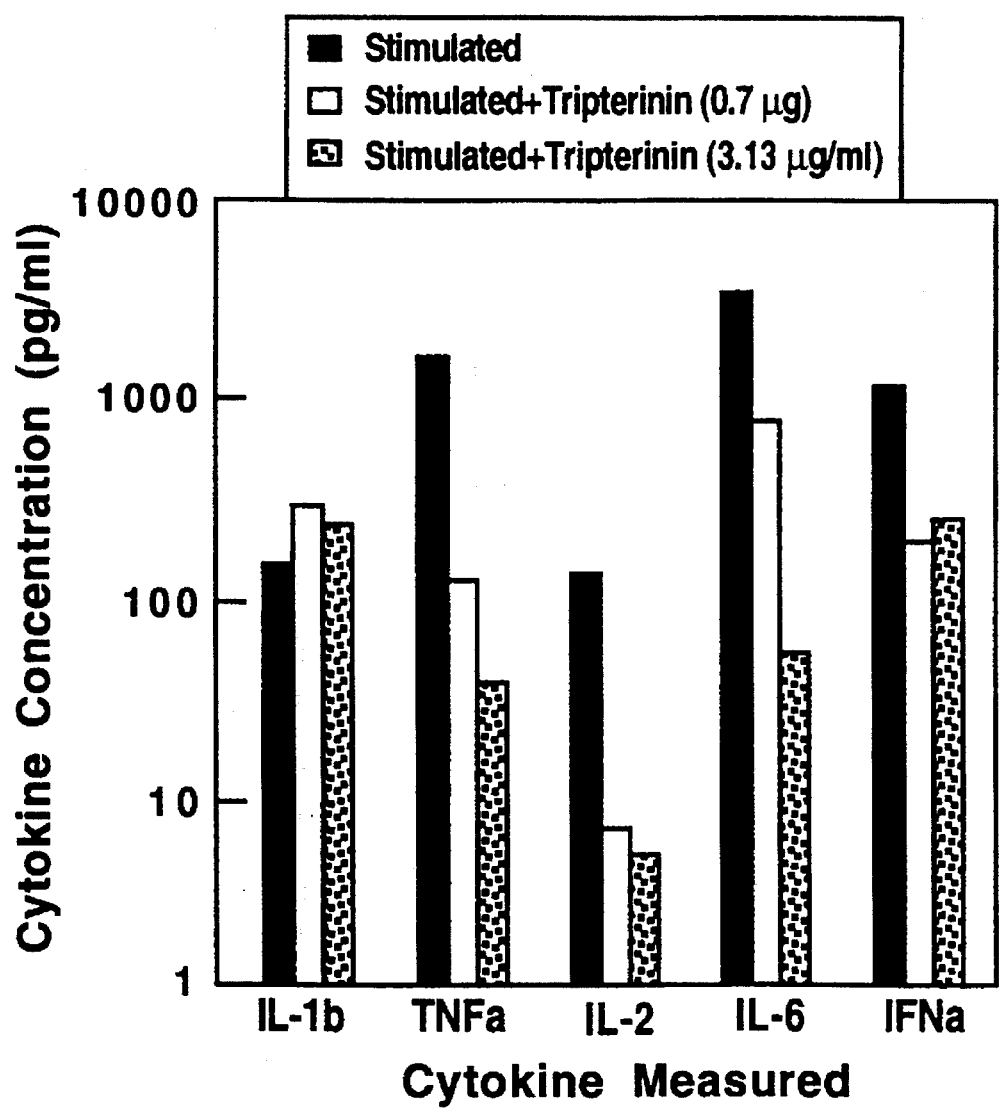
FIG. 12 shows the effect of 0.7 µg/ml tripterinin (crosshatched bars), 3.13 µg/ml tripterinin (shaded bars) and vehicle alone (solid bars) on the production of IL-1b, TNFα, IL-2, IL-6 and IFNγ by PHA activated human peripheral blood lymphocytes in culture.

As shown in FIG. 12, tripterinin inhibited the production of TNFα, IL2, IL-6, and IFNγ, with the medium concentration of these cytokines being decreased by 93%, 96%, 83% and 84%, respectively, in the presence of 0.7 µg/ml tripterinin. The production of TNFα, IL2, IL-6, and IFNγ decreased by 98%, 96%, 99% and 80%, respectively, in the presence of 3.13 µg/ml tripterinin. The compound did not significantly affect IL-1B production.

E. Cytotoxicity

Potential cytotoxicity of tripterinin was assessed by measurement of the effect of the compound on reduction of MTT (3-[4,5-Dimethylthiazol-2-yl]-2,5-diphenyltetrazolium bromide) by cultured cells, an index of cellular respiration and a sensitive assay for the detection of cytotoxicity (Green, et al.). Toxicity was evaluated in vitro in human PBLs and in mouse thymocytes, as detailed in Example 7. Sodium azide was used as a cytotoxic control. Cytotoxicity was also assessed using the standard method of trypan blue dye staining. Tripterinin showed no significant toxicity below a tissue culture medium concentration of 10 µg/ml, the highest concentration tested.

III. Treatment Method

In one embodiment, the treatment method of the invention is directed toward the treatment of patients with an autoimmune condition characterized by elevated activity levels of IL-1, TNFα, and IL-6. The elevated activity level may be due to increased level of cytokine or reduced level of endogenous cytokine agonist, or a combination of the two. Thus, an elevated activity level of IL-1 in the patient's serum or synovial fluid may be due to an above-normal concentration of IL-1 and/or a below-normal activity level of endogenous IL-1 inhibitor, as measured, for example, by the ability of the serum or synovial fluid to stimulate cell proliferation in IL-1-responsive lymphocytes in vitro, as described below.

Table 2 shows a list of autoimmune diseases, including RA, which may be characterized by above-normal activity levels of IL-1, IL-6, and/or TNFα. The relationship between a given disease state and activity levels of IL-1, IL-6, and/or TNFα can be tested for individual patients, where necessary, or preferably is established with reference to clinical studies involving groups of patients with known types of autoimmune disease.

TABLE 2

| Autoimmune Diseases | |
|---|---|
| Disease | Tissue Affected |
| Addison's disease | adrenal |
| Allergies | inflammatory cells |
| Asthma | bronchi |
| Atherosclerosis | vessel walls |
| Crohn's disease | intestine |
| Diabetes (Type I) | pancreas |
| Graves' disease | thyroid |
| Guillain-Barr"'Syndrome | nerve cells |
| Lupus erythematosis | multiple tissues |
| Multiple sclerosis | nerve cells |
| Myasthenia Gravis | neuromuscular junction |
| Psoriasis | skin |
| Primary biliary cirrhosis | liver |
| Rheumatoid arthritis | joint lining |
| Uveitis | eye |

In a general treatment method, the composition of the invention, comprising tripterinin alone or in combination with cyclosporin A, azathioprine, methotrexate, or a glucocorticoid, is administered in an amount sufficient to lower the serum or synovial fluid activity levels of one of the elevated cytokines, i.e., IL-1, IL-6, or TNFα. The lowering of cytokine activity level may be measured directly in the treated patient, or the reduction in cytokine activity level may be projected from clinical studies in which dose regimens useful in achieving such reduction are established.

The composition may be administered by oral or parenteral administration, such as IV administration. For oral administration, the compound may be given in tablet or capsule form, at a preferred dose of 1 to 25 mg/kg patient body weight per day. The dose may be increased or decreased appropriately depending on the response of the patient, and patient tolerance.

A parenteral suspension can be administered by injection, e.g., intravenously, intramuscularly, or subcutaneously. A dose between about 0.1 to 1 mg tripterinin/kg body weight per day is preferred, and this level may be increased or decreased appropriately, depending on the conditions of disease, the age of the patient, and the ability of the patient to resist infection.

The method is applicable to autoimmune diseases, such as those given in Table 2 above. In the treatment method, the patient is given the compound on a periodic basis, e.g., 1–2 times per week at a dosage level sufficient to reduce symptoms and improve patient comfort.

In a more specific embodiment, the invention is used in treating rheumatoid arthritis. As above, the patient is administered a dose of tripterinin, either alone or in combination with cyclosporin A, azathioprine, methotrexate, or a glucocorticoid, in an amount sufficient to lower the serum or synovial fluid activity levels of one of the elevated cytokines, either IL-1, IL-6, or TNFα. The drug doses and timing of the doses, and where necessary, the monitoring of IL-1, IL-6, and/or TNFα activity levels are as described above.

The invention also includes a method for the treatment of transplantation rejection of cardiac, kidney, liver, and bone marrow transplants, by administering to the patient, tripterinin or tripterinin in combination with cyclosporin A, azathioprine, methotrexate, or a glucocorticoid. Initial treatment is administered perioperatively. In addition, the composition may be administered chronically to prevent graft rejection. Finally, the compound may also be used to treat episodes of late graft rejection. It is anticipated that the dose and the administration regimen will be different in each of the three cases.

The treatment is typically started perioperatively, and is continued on a daily dosing regimen, for a period of at least several weeks, for treatment of acute transplantation rejection. During the treatment period, the patient may be tested periodically for immunosuppression level, e.g., by testing the ability of the patient's lymphocytes to mount a mixed lymphocyte response against allogenic lymphocytes.

The following examples illustrate the method for obtaining tripterinin, and demonstrate various physical, chemical, and in vitro properties of the compound. The examples are intended to illustrate, but in no way limit the scope of the invention.

EXAMPLE 1

Preparation of Tripterinin

*Tripterygium wilfordii* plants were obtained in Taiwan or in Fujian Province, China. Plants were air dried in sunlight. The root xylem of the plant (300 g) was ground into a crude powder and extracted with 5 volumes (1.5 l) of 95% ethanol, under reflux at 85° C. for 4 hours. The filtered xylem powder was then extracted two more times in 3 volumes (900 ml total) of 95% ethanol. The three extracts (total of about 3.3 l) were combined and the resulting mixture was concentrated at 50° C. under vacuum, to about 2% of the original volume, i.e., about 66 ml. The ethanol extract syrup obtained was then diluted with 33 ml water, and filtered through Whatman #1 filter paper. The filtrate was extracted 4 times (50 ml/extraction) with methylene chloride. The combined filtrate (about 200 ml) was concentrated, and applied to a 1 cm (diameter)×5 cm column containing silica gel (1.5 kg; 60–200 mesh). The column was washed successively with 100 ml methylene chloride, and 100 ml methylene chloride:methanol (95:5). The fraction which eluted in 95:5 solvent contained about 0.3 g material, and is referred to herein as a 1:1000 extract.

Forty grams of the material prepared as above (in scale-up) was concentrated to a small volume in 20 ml acetone. The solution was applied to a 13 cm×14 cm column containing silica gel (800 gm; 60–200 mesh) and eluted with a methylene chloride:methanol 97:3 to produce six one liter fractions. The yield of each fraction was about 5% or 2 grams. Fractions 2–5 were combined and the resulting 8 grams of material, the 1:5000 extract, was then applied to a 8 cm×40 cm column containing silica gel (320 gm; 260–400 mesh) and eluted with methylene chloride:methanol (97:3) to produce five 300 ml fractions. Fractions 2–4, which were yellowish in color, were combined. The solvent was removed by evaporation under vacuum to yield 4 grams of light brown powder, the purified (1:10,000) TW extract.

The 1:10,000 extract from above was dissolved in 1 ml methylene chloride, applied to a Lobar column (Type B, Si 60) and eluted with hexane:methylene chloride:methanol (1:1:0.15). Twenty-four fractions were collected. Crystalline tripterinin appeared in fractions 17 and 18. The compound was recrystallized in acetone:ethyl ether. Yield of the final step was 0.78%; 640 mg of the 1:10,000 extract yielded 5 mg of white needles, melting point 450° C.

EXAMPLE 2

Physical Characteristics of Tripterinin

A. Mass Spectrometry

A Hewlett-Packard GC/MS instrument with a 5890 Series II gas chromatograph and a 5971 mass selective detector was utilized. The compound showed the high resolution mass spectrum shown in FIG. 3, discussed above.

B. NMR

Proton NMR (nuclear magnetic resonance), $^{13}$C NMR and COSY NMR spectra were obtained using a 300 MHZ General Electric QE Plus instrument. The sample was dissolved in spectral grade deuterochloroform; TMS (tetramethylsilane) was used as the internal standard. All of the values are given in ppm. The $^{13}$C NMR and proton NMR spectra are shown in FIG. 5, and in FIGS. 6A and 6B, respectively, as discussed above.

C. Infared

The infared spectrum of the compound was obtained using a Perkin Elmer 1620 FT-IR instrument. The sample was dissolved in spectral grade chloroform. The spectrum (FIG. 4) is discussed above.

D. Thin Layer Chromatography

One microgram samples of the extracts or a 10 microgram sample of tripterinin were applied to a silica gel coated aluminum thin layer chromatography plate (Whatman, catalog #4420 222). The development solvent system was hexane:methylene chloride:methanol in volume ratios of 1:1:0.15. Following separation, samples were visualized using an ultraviolet lamp or by application of an aerosol of 0.5% vanillin in $H_2SO_4$:ethanol (4:1).

TLC profiles of the various TW extracts and of tripterinin are shown in FIG. 2. Lane A shows the 1:1,000 extract; lane B shows the 1:5,000 extract; lane C shows the 1:10,000 extract; and Lane D shows tripterinin.

EXAMPLE 3

Suppression of PBL Proliferation in vitro

A. Human Peripheral Blood Lymphocyte (PBL) Preparation

Human peripheral blood lymphocytes were prepared using an established method (Boyum). Human blood buffy coat samples, approximately 25 ml/donor, were obtained from the Stanford University Medical Center Blood Bank. Using sterile technique, the buffy coat samples were gently resuspended in a total volume of 100 ml with the addition of calcium and magnesium free Hank's balanced salt solution (HBSS, obtained from Gibco) at room temperature. A volume of 25 ml of the cell suspension was then layered onto 15 ml of Ficoll-Pacque (Pharmacia LKB Biotechnology, Inc.) in a 50 ml conical centrifuge tube. Tubes were centrifuged in a Beckman GPR tabletop centrifuge (GH-3.7 Rotor) at 400×g for 30 minutes at 15° C.

Following centrifugation, the PBL suspensions at the interfaces were transferred to new 50 ml tubes using a transfer pipette, and the PBL samples were resuspended in a total volume of 45 ml HBSS and centrifuged at 354×g for 10 minutes at 15° C. Supernatants were discarded. PBL's were resuspended in 10 ml HBSS, combined to make a total of 45 ml HBSS, and centrifuged at 265×g for 10 minutes at 15° C. The cell pellets were suspended in 10 ml of X-Vivo tissue culture medium (Bio Whittaker) and counted using a hemocytometer. Tissue culture medium was then added to achieve a final cell concentration of 1× $10^6$ cells/ml. Additional dilutions were carried out as required for each assay.

Assays were carried out in 96 well sterile tissue culture plates (Costar 3790 and Costar 3595). A volume of 150 µl of X-Vivo medium or sterile distilled water was added to the outer wells of the plate to prevent evaporation of medium within the experimental wells. PBL's from 2 different donors were used in parallel in all experiments. A volume of 100 µl PBL suspension was added to each well using a multichannel pipette. Plates were incubated in an atmosphere of 93% air/7% $CO_2$ in a tissue culture incubator at 37° C. X-35 (AMAC #0178), an anti CD-3 surface antigen antibody, was used at 5 ng/ml to stimulate PBL proliferation.

Tripterinin or tripterifordin was dissolved in ethanol (10 mg/ml) and then diluted in sterile X-Vivo tissue culture medium to obtain the final concentrations required for each experiment.

Four hours prior to the conclusion of incubation, 50 µl of X-Vivo tissue culture medium containing 8 µCi/ml [$^3$H] Thymidine (Amersham, 49 Ci/mmol) was added to each tissue culture well. After 72 hours total incubation time, the cells were removed from the tissue culture wells and applied to filter paper using a cell harvester (Brandel Model MB-24). The filter paper was dried for one hour under a heat lamp and then cut into 1 cm discs. Each sample was placed in a scintillation vial containing 2 ml of scintillation fluid (Biosafe, Research Products International Corp.). Samples were counted in a Beckman LS 6000SC scintillation counter.

As shown in FIG. 8 and discussed above, tripterinin inhibited PBL proliferation in both stimulated and unstimulated cultures. Half maximal inhibition occurred at a concentration of approximately 0.5 µg/ml. Tripterifordin showed little or no inhibitory effect (FIG. 9).

EXAMPLE 4

Inhibition of IL-1 Action on Mouse Thymocytes

Mouse thymocytes were prepared, and the action of IL-1, which stimulates thymocyte proliferation, was measured using standard techniques (O'Gara). Three to six week old C3H/HeN mice were obtained from Simonsen Laboratories, Gilroy, Calif. and sacrificed by $CO_2$ inhalation. Thymi were removed, separated from adherent non-thymic tissue, homogenized in Hank's balanced salt solution (Gibco) using a glass homogenizer, and centrifuged at 180×g for 10 minutes at 15° C. Following an additional wash in HBSS, the thymocytes were resuspended in RPMI 1640 tissue culture medium (Gibco) containing 50 µM 2-mercaptoethanol (Fisher), 2 mM glutamine (Gibco), 1 mM sodium pyruvate, non-essential amino acids, penicillin (100 U/ml) streptomycin (100 µg/ml), 10% heat inactivated fetal bovine serum and Phytohemagglutinin (PHA, Pharmacia, final concentration 10 µg/ml). Cells were cultured in round-bottom 96 well microtiter tissue culture plates, 6×$10^5$ cells per well in a volume of 100 µl. Tripterinin or tripterifordin was diluted in tissue culture medium and added to the wells in the presence and absence of IL-1 (recombinant human IL-1, R&D Systems catalog #201-LB, 0.1 ng/ml). Total volume was 150 µl per well.

Plates were incubated for 72 hours (95% air/5% $CO_2$, 37° C.). During the last four hours of incubation, [$^3$H]-thymidine (Amersham, 49 Ci/mM) was added (0.5 µCi per well). Cells were harvested onto Whatman 934-AH glass microfiber filters and counted in a Beckman LS 6000 scintillation counter. Results were expressed as counts per minute per well.

Untreated cells showed minimal DNA synthesis (thymidine incorporation 80 cpm/well). PHA alone stimulated thymidine incorporation 2–3 fold. Treatment with 0.1 ng/ml IL-1 in the presence of PHA resulted in a 60 fold increase. Addition of the tripterinin resulted in a dose dependent inhibition of IL-1 stimulation, as shown in FIG. 10. Inhibition was measured over a range of 0.02 to 1 µg/ml. Half-maximal inhibition occurred at 0.1 µg/ml. Tripterifordin failed to inhibit the cell-proliferative effect of IL-1, even at a concentration of about 3 µg/ml.

EXAMPLE 5

Inhibition of IL-2 Action by Tripterinin

The effect of tripterinin on the action of IL-2 was assessed by measurement of the compound's ability to inhibit IL-2 stimulated growth of the IL-2 dependent cell line HT-2, a well-established biological assay of IL-2 action (O'Gara). HT-2 cells were cultured in 75 cm$^2$ (Corning) tissue culture flasks in RPMI 1640 medium containing 10% fetal bovine serum (Hyclone), 50 µM 2-mercaptoethanol (Fisher), 10 U/ml recombinant human IL-2 (Cetus), 20 mM HEPES, 2 mM glutamine, 100 U/ml penicillin and 100 µg/ml streptomycin. Cells were passaged every 2 days. For experiments, HT-2 cells were centrifuged at 180×g for 10 minutes, washed twice with 10 ml of IL-2 free culture medium and resuspended in RPMI 1640 medium prepared as above, except containing 5% fetal bovine serum. Final cell concentration was 1×$10^4$/well. Cultures were incubated with varying concentrations of the tripterinin (95% air/5% $CO_2$, 37° C.) for 20 hours. Tritiated thymidine, 0.5 µCi/well (Amersham, 49 Ci/mmol), was added and the incubation carried out for an additional 4 hours. Cells were harvested and counted as described for the PBL proliferation assay.

As shown in FIG. 11, tripterinin, over a concentration range of 0 to 0.78 µg/ml, produced over a 10-fold inhibition IL-2 induced DNA synthesis. Half maximal inhibition occurred at 0.2 µg/ml.

EXAMPLE 6

Effect of Tripterinin on Cytokine Production

Human PBLs were prepared and incubated in the presence of PHA as in Example 3. The cells were incubated in the presence and absence of tripterinin (0.7 or 3.13 µg/ml). Samples of tissue culture medium were collected following 24 hours incubation and stored at −70° C. prior to assay.

Cytokine measurements were carried out using commercially available ELISA assay kits (R&D Systems), in accordance with the supplier's protocols. In brief, 100 µl of the assay buffer supplied was added to each of the wells of a microtiter plate containing pre-bound anti-cytokine antibody, followed by 100 µl of standard or sample solution, diluted appropriately for the concentration range measured. All incubations were carried out at 37° or 24° C., per the supplier's protocol.

Following two hours incubation, the plates were washed four times with assay buffer, and the second antibody, anti-anti-cytokine-horseradish peroxidase (HRP), was added to each well in a volume of 200 µl. Following another 2 hour incubation, the wells were washed four times with buffer, and 200 µl/well HRP substrate was added. After 20 minutes incubation, the reaction was terminated by the addition of 50 µl $H_2SO_4$ to each well. Optical density was determined using a Molecular Devices microtiter plate reader. Results were calculated as pg cytokine/ml medium, as shown in FIG. 12.

EXAMPLE 7

Evaluation of Potential Cytotoxicity

Potential cytotoxicity of tripterinin was assessed by measurement of the compound's effect on the reduction of MTT (3-[4,5-Dimethylthiazol-2-yl]-2,5-diphenyltetrazolium bromide) by cultured cells. MTT, a yellow-colored compound, is reduced by mitochondrial enzymes to form a purple crystalline reduction product (formazan), providing an index of cellular respiration as well as a sensitive assay for cytotoxicity (Green, et al.).

Cytotoxicity was assessed in cultured human PBLs and mouse thymocytes. A stock solution of MTT (Sigma), 5 mg MTT/ml phosphate buffered saline, pH 7.4, was prepared and stored in the dark at 4° C. Following 21 hours incubation under conditions identical to those above, 25 µl of MTT solution was added to each culture well. After an additional 3 hour incubation, the experiment was terminated by addition of a solution of 10% sodium dodecyl sulfate in 0.01N HCl. Following overnight incubation at 37° C. (to solubilize the formazan crystals, the MTT reduction product), optical density was determined at 570–650 nm in a Molecular Devices microtiter plate reader. Data are expressed as the ratio of the optical density of the tripterinin treated sample to that of untreated controls. No significant toxicity was observed at concentrations up to 10 µg/ml, the highest dose tested. The standard method of trypan blue vital dye staining was also used to assess toxicity. Results were consistent with those from the MTT reduction assay.

Although the invention has been described with respect to particular methods and applications, it will be appreciated that various changes and modifications may be made without departing from the spirit of the invention.

It is claimed:

1. A purified compound having the structural formula:

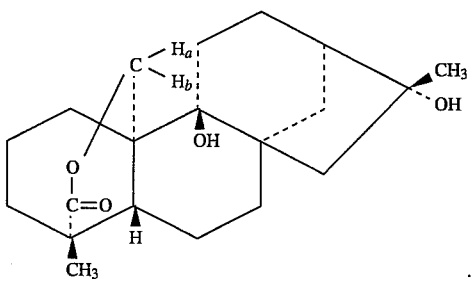

2. A pharmaceutical composition useful in immunosuppression treatment, said composition consisting essentially of a compound having the structural formula:

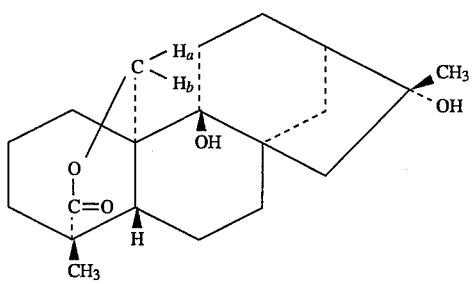

in a pharmaceutically acceptable delivery vehicle.

3. A method of treating rheumatoid arthritis in a patient, comprising administering to the patient the composition of claim 2 in an amount effective to reduce serum or synovial fluid activity levels of one or more of the cytokines IL-1, TNFα, or IL-6.

4. The method of claim 3, wherein said administering includes injecting the composition into the joints of the patient.

5. The method of claim 3, wherein said administering includes injecting the composition intravenously into the patient, in an amount effective to achieve a serum concentration of said compound of between about 0.05–0.3 µg/ml.

6. The method of claim 3, wherein said administering is by oral administration, in a dosage amount effective to achieve a serum concentration of said compound of between about 0.05–0.3 µg/ml.

7. The method of claim 3, wherein said administering is repeated at intervals of at least 24 hours, over a several week period following the onset of symptoms of the disease in the patient.

* * * * *